(12) United States Patent
Cantwell et al.

(10) Patent No.: US 6,322,998 B1
(45) Date of Patent: Nov. 27, 2001

(54) **RECOMBINANT DNA COMPOUNDS THAT ENCODE ACV SYNTHETASE ACTIVITY OF *CEPHALOSPORIUM ACREMONIUM***

(75) Inventors: Cathleen A. Cantwell; Roland L. Hodges; JoAnn Hoskins; Stephen W. Queener, all of Indianapolis; Paul L. Skatrud, Greenwood, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 07/968,620

(22) Filed: Oct. 29, 1992

Related U.S. Application Data

(63) Continuation of application No. 07/532,466, filed on Jun. 1, 1990, now abandoned.

(51) Int. Cl.[7] .......................... C12P 21/00; C12N 15/80; C12N 15/79; C12N 15/63
(52) U.S. Cl. .................. 435/69.1; 435/455; 435/456; 435/320.1; 435/471; 536/23.1; 536/23.2; 536/23.5; 536/23.7
(58) Field of Search .................. 435/172.3, 69.1, 435/320.1, 455, 456, 471; 536/27, 23.1, 23.2, 23.5, 23.7

(56) References Cited

U.S. PATENT DOCUMENTS 4,885,252 * 12/1989 Ingolia et al. .................... 435/252.3

FOREIGN PATENT DOCUMENTS 0320272    6/1989  (EP).

OTHER PUBLICATIONS

Smith et al. EMBO J. 9:741 (1990).

* cited by examiner

*Primary Examiner*—David Guzo
(74) *Attorney, Agent, or Firm*—Charles E. Cohen; Paul R. Cantrell

(57) ABSTRACT

The present invention provides DNA compounds that encode ACV synthetase activity of *Cephalosporium acremonium*. The compounds can be used to construct recombinant DNA expression vectors for a wide variety of host cells, including *E. coli*, Penicillium, Cephalosporium, and Aspergillus.

34 Claims, 9 Drawing Sheets

Beta-Lactam Biosynthesis

RECOMBINANT DNA COMPOUNDS THAT ENCODE ACV SYNTHETASE ACTIVITY OF *CEPHALOSPORIUM ACREMONIUM*

This application is a continuation of application Ser. No. 07/532,466, filed Jun. 1, 1990, now abandoned.

BACKGROUND OF THE INVENTION

Beta-lactam antibiotics are among the most important clinically, and the isolation of novel β-lactam compounds continues six decades after the discovery of the penicillins by Fleming. The common structural feature of the penicillins and cephalosporins (including cephamycins) is the β-lactam ring.

These antibiotics are produced by a variety of prokaryotes and lower eukaryotes. The penicillins, exemplified by the compounds penicillin G (benzyl-penicillin) or penicillin V, are produced by filamentous fungi, most notably *Penicillium chrysogenum*. The cephalosporins, first isolated as a product from the lower eukaryote, *Cephalosporium acremonium* (syn. *Acremonium chrysogenum*), are also metabolites of many prokaryotes, especially *Streptomyces clavuligerus, S. lipmanii* and *S. cattleya*, that also produce cephamycins and other β-lactams such as oxypenams (clavulanic acid) and carbapenems (thienamycin).

The development of cell-free systems from β-lactam-producing organisms has allowed the establishment of the biosynthetic steps in the pathway of the sulfur-containing β-lactams (penicillins and cephalosporins).

The initial steps in the formation of penicillins in filamentous fungi (e.g., *P. chrysogenum*), and the cephalosporins produced by both prokaryotes (e.g., *S. clavuligerus*) and lower eukaryotes (e.g., *C. acremonium*), are identical. ACV synthetase catalyzes the condensation of the amino acid precursors L-α-aminoadipate, L-cysteine, and L-valine to the tripeptide LLD-ACV. The next step forms the first β-lactam in the pathway by the cyclization of the tripeptide yielding isopenicillin N (IPN), a precursor to all penicillins, cephalosporins and cephamycins.

After synthesis of IPN, the pathways to cephalosporins and penicillins diverge. In *P. chrysogenum*, for example, the α-aminoadipyl side chain of IPN can be exchanged for one of many (nearly 100 to date) hydrophobic side chains derived from the corresponding acyl CoA. One of the most familiar examples is the formation of penicillin G (benzylpenicillin) from phenylacetyl CoA and IPN. However, in the fungus *C. acremonium*, the α-aminoadipyl side chain is isomerized to produce penicillin N. The five-membered thiazolidine ring of the penicillin is then "expanded" to the six-membered dihydrothiazine ring that is characteristic of the cephalosporins. This reaction is catalyzed by deacetoxycephalosporin C synthetase (DAOCS) and produces the first cephalosporin in the pathway, deacetoxycephalosporin C (DAOC).

The present invention provides DNA compounds comprising an isolated DNA sequence encoding an activity involved in the production of penicillins and cephalosporins, said activity being referred to as δ-(L-α-aminoadipyl)-L-cysteinyl-D-valine (ACV) synthetase. The present invention expands the repertoire of beta-lactam biosynthetic enzymes which can be overproduced. This ability facilitates the bioconversion of substrate analogs to novel beta-lactams and strain improvement by increased gene dosage.

SUMMARY OF THE INVENTION

The present invention comprises DNA sequences that encode the enzyme ACV synthetase of *Cephalosporium acremonium*. The enzyme catalyzes the condensation of the amino acid precursors L-α-aminoadipate, L-cysteine, and L-valine to the tripeptide δ-(L-α-aminoadipyl)-L-cysteinyl-D-valine (ACV). The reaction is a critical step in the biosynthesis of the beta-lactam antibiotics. This pathway is depicted in FIG. 1.

The DNA compounds of the present invention encode the ACV synthetase enzyme of *Cephalosporium acremonium*. A preferred DNA compound of the invention that encodes the ACV synthetase activity was isolated from *Cephalosporium acremonium* genomic DNA. The cloned ACV synthetase gene is useful for increasing the yield of penicillins and cephalosporins in fungi, particularly if the reaction catalyzed by ACV synthetase is the rate-limiting step. This is accomplished by increasing the gene dosage or placement of the coding region behind a strong promoter.

The DNA compound that encodes the ACV synthetase activity can be used to construct recombinant DNA expression vectors. Four types of these expression vectors are especially useful: the first drives high-level expression of the ACV synthetase protein in *E. coli*; the second in Penicillium; the third in Aspergillus; and the fourth in Cephalosporium.

The following section provides a more detailed description of the present invention. For purposes of clarity and as an aid in the understanding of the invention the following items are defined below.

AmR—the apramycin resistance-conferring gene.

ApR—the ampicillin resistance-conferring gene; also used to denote the ampicillin-resistant phenotype.

bp—a base pair of double-stranded DNA.

cLEU2p—Cephalosporium LEU2 promoter.

cpcbCp—the Cephalosporium IPNS promoter.

HPT—hygromycin B phosphotransferase coding region.

IPNS—isopenicillin N synthetase.

Isopenicillin N synthetase—an enzyme, also known as cyclase or IPN cyclase, that catalyzes the formation of isopenicillin N from δ-(L-α-aminoadipyl)-L-cysteinyl-D-valine.

Isolated DNA compound—Any DNA sequence, however constructed or synthesized, which is locationally distinct from its natural location in genomic DNA. The definition includes the isolated DNA sequence in all its forms other than the natural state. For example, the DNA sequence may be inserted into a plasmid or phage vector or inserted into the genome of the organism from which it came or any other organism to increase the gene dosage.

lacZα—the promoter and β-galactosidase (lacZ) α-fragment derived from the *E. coli* lac operon.

ORI—a plasmid or vector origin of replication, the DNA sequence that serves as an attachment or start site for DNA polymerase.

pcbc—the IPNS gene.

phlR—the phleomycin resistance gene.

ppcbC ORF—the IPNS coding sequence.

ppcbCp—the Penicillium IPNS promoter.

BRIEF DESCRIPTION OF THE FIGURES

The restriction site and function maps presented in the accompanying drawings are approximate representations of the recombinant DNA vectors discussed herein. The restriction site information is not exhaustive; therefore, there may be more restriction sites of a given type on the vector than actually shown on the map.

DETAILED DESCRIPTION OF THE INVENTION

Figure 1:
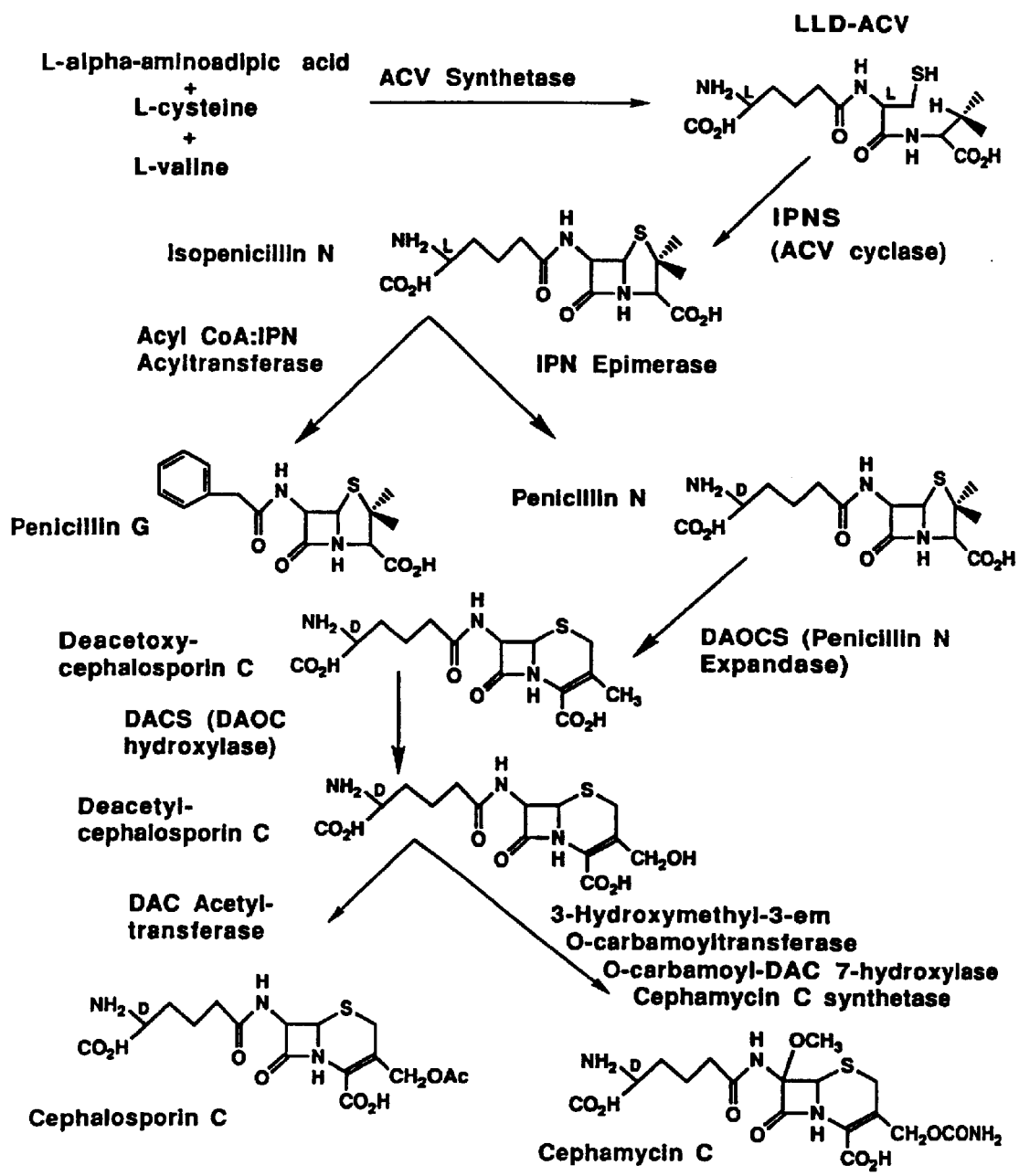
FIG. 1. The beta-lactam biosynthetic pathway.

The present invention comprises an isolated DNA compound that comprises a DNA sequence encoding ACV synthetase activity of *Cephalosporium acremonium*. The present invention also comprises DNA compounds and recombinant DNA cloning and expression vectors that encode the ACV synthetase activity of *C. acremonium*.

The *Cephalosporium acremonium* ACV synthetase gene can be isolated on an ~12 kb EcoRI-SalI fragment derived from plasmid pPS97, which has been deposited with the Northern Regional Research Laboratories (NRRL), 1815 North University Street, Peoria, Ill. 61604, on May 11, 1990 in *E. coli* K12 DH5α under the accession number NRRL B-18653.

Plasmid pPS97 serves as useful starting material for the construction of other expression vectors of the invention. These vectors are especially useful in a method for producing ACV synthetase activity in a recombinant host cell, said method comprising: (1) transforming said host cell with a recombinant DNA expression vector that comprises: (a) a promoter and translational activating sequence; and (b) a DNA sequence that encodes ACV synthetase activity and is positioned for expression from said promoter and translational activating sequence; and (2) culturing said host cell transformed in step (1) under conditions that allow for expression of said ACV synthetase activity.

The ACV synthetase expression vectors of the present invention are not limited to a particular selectable marker. Those skilled in the art recognize that many selectable markers are suitable for use on ACV synthetase expression vectors. Such selectable markers for *E. coli* include, for example, genes that confer kanamycin resistance, genes that confer chloramphenicol resistance, or other antibiotic resistance-conferring genes. In Aspergillus, Cephalosporium and Penicillium, useful markers include the phleomycin resistance gene (phlR) and the gene encoding hygromycin B phosphotransferase. Expression vectors containing the ampicillin resistance gene are less useful because the gene encodes beta-lactamase, which, if expressed, will interfere with reactions producing beta-lactam antibiotics.

The present invention is not limited to the particular vectors exemplified herein. Instead, the present invention comprises DNA compounds that encode the ACV synthetase activity of *C. acremonium*. The DNA compounds of the present invention can be used to construct expression vectors that drive expression of *C. acremonium* ACV synthetase activity in any host cell in which the expression vector replicates or integrates and in which the promoter and translational activating sequence are functional.

Therefore, the present invention comprises any *E. coli* expression plasmid or vector comprising a promoter that drives expression of *C. acremonium* ACV synthetase activity in *E. coli*. The present invention comprises expression vectors that drive expression of *C. acremonium* ACV synthetase activity and utilize a replicon functional in *E. coli*, such as, for example, a replicon from such plasmids as pBR322, pACYC184, F, ColV-K94, R1, R6-5, or R100. Nor is the present invention solely limited to plasmid vectors, for the present invention also comprises expression vectors that express the ACV synthetase protein and utilize integration or viral replication to provide for replication and maintenance in the host cell.

The present invention is not limited to a particular promoter and translational activating sequence to drive expression of the ACV synthetase gene. The present invention comprises the use of any promoter and translational activating sequence that function in *E. coli* and are used to express ACV synthetase protein in *E. coli*. Many promoter and translational activating sequences functional in *E. coli* are known and are suitable for driving expression of ACV synthetase protein in *E. coli*. Such transcriptional and translational activating sequences include, but are not limited to, the lpp, lac, trp, tac, λpL, and λpR promoter and translational activating sequences.

In addition, transcriptional and translational activating sequences from other organisms can be ligated, by in vitro enzyme ligation or in vivo recombination, to the present ACV synthetase activity-encoding DNA compounds that drive expression of ACV synthetase activity in host cells. Vectors that drive expression of ACV synthetase activity in host cells other than *E. coli* are also useful, especially for purposes of increasing the antibiotic producing ability and efficiency of a given organism. Useful Cephalosporium promoters include the promoters of the DAOCS/DACS and IPNS genes. In Penicillium, the promoter of the *P. chrysogenum* IPNS gene may be used to drive expression. Alternatively, the host cell can be transformed with an ACV synthetase-encoding vector lacking signals driving ACV synthetase expression.

A variety of organisms produce β-lactam antibiotics. The following Table presents a non-comprehensive list of β-lactam antibiotic-producing organisms.

TABLE I

| β-Lactam Antibiotic-Producing Organisms | |
|---|---|
| Organism | Antibiotic |
| Agrobacterium | various β-lactams |
| Arachnomyces minimus | penicillins and cephalosporins |
| Anixiopsis peruviana | penicillins and cephalosporins |
| Aspergillus | penicillins |
| Cephalosporium | |
| acremonium | penicillins and cephalosporins |
| purpurascens | |
| polyaleurum | |
| chrysogenum | |
| curtipes | |
| Chromobacterium | various β-lactams |
| Emericellopsis terricola | penicillins and cephalosporins |

TABLE I-continued

β-Lactam Antibiotic-Producing Organisms

| Organism | Antibiotic |
| --- | --- |
| minima | |
| synnematicola | |
| glabra | |
| mirabilis | |
| salmosynnemata | |
| Flavobacterium | various β-lactams |
| Gluconobacter | various β-lactams |
| Nocardia | |
| lactamadurans | cephamycin C |
| uniformis | nocardicin |
| Paecilomyces | penicillins and |
| carneus | cephalosporins |
| persicinus | |
| Penicillium | |
| chrysogenum | various penicillins and other β-lactams |
| Serratia | various β-lactams |
| Spiroidium | penicillins and |
| fuscum | cephalosporins |
| Streptomyces | |
| antibioticus | clavulanic acid |
| argenteolus | asparenomycin A, MM 4550, and MM 13902 |
| cattleya | thienamycin |
| chartreusis | SF 1623 and cephamycin A and B |
| cinnamonensis | cephamycin A and B |
| clavuligerus | PA-32413-I, cephamycin C, A16886A, penicillins, cephalosporins, clavulanic acid, and other clavams |
| fimbriatus | cephamycin A and B |
| flavovirens | MM 4550 and MM 13902 |
| flavus | MM 4550 and MM 13902 |
| fulvoviridis | MM 4550 and MM 13902 |
| griseus | cephamycin A and B and carpetimycin A and B |
| halstedi | cephamycin A and B |
| heteromorphus | C2081X and cephamycin A and B |
| hygroscopicus | deacetoxy-cephalosporin C |
| lipmanii | cephamycin, penicillin N, 7-methoxycephalosporin C, A16884, MM4550, MM13902 |
| olivaceus | epithienamycin F, MM 4550, and MM 13902 |
| panayensis | C2081X and cephamycin A and B |
| pluracidomyceticus | pluracidomycin A |
| rochei | cephamycin A and B |
| sioyaensis | MM 4550 and MM 13902 |
| sp. OA-6129 | OA-6129A |
| sp. KC-6643 | carpetimycin A |
| tokunomensis | asparenomycin A |
| viridochromogenes | cephamycin A and B |
| wadayamensis | WS-3442-D |

Some of the foregoing β-lactam antibiotic-producing organisms are used in the pharmaceutical industry for purposes of antibiotic production. The antibiotic-producing ability of these organisms can be increased and made more efficient by increasing the intracellular concentration of the antibiotic biosynthetic enzymes during the fermentation. A demonstration of using a β-lactam biosynthetic gene in this manner is presented in Skatrud et al., *Bio/Technology* 7:477 (1989). The ACV synthetase activity-encoding DNA compounds of the present invention can be used to construct expression vectors that, when transformed into the appropriate host cell, increase the intracellular concentration of ACV synthetase activity of the transformed host cell and thereby increase the antibiotic-producing ability and efficiency of that cell.

A vector that will increase the intracellular concentration of ACV synthetase activity of a given host cell into which the vector is transformed requires the following elements: 1) an ACV synthetase activity encoding DNA compound of the present invention; and 2) a promoter and translational activating sequence that not only function in the host cell to be transformed, but also are positioned in the correct orientation and position to drive expression of the ACV synthetase activity encoding DNA. of course, stable transformants can only be obtained if the vector replicates, either as an extrachromosomal element or integrated in the genomic DNA, in the host cell. Thus, a preferred vector contains sequences that specifically direct replication or integration of the vector in the host cell. However, the presence of such specific replication or integration sequences is not absolutely required, as non-specific integration may occur when DNA is introduced into a host cell. An ACV synthetase expression vector could also comprise an antibiotic resistance conferring gene or some other element that provides a means of selecting for host cells which contain the vector, but such selectable elements may neither be necessary nor desired when the vector integrates into the chromosomal DNA of the host cell.

By providing the coding sequence of the ACV synthetase gene of *Cephalosporium acremonium*, the present invention provides ACV synthetase expression vectors for any organism susceptible to transformation. The *E. coli* ACV synthetase expression vectors described above illustrate the wide variety of expression vectors of the present invention. However, many of the preferred vectors of the invention are designed to drive expression of ACV synthetase in a β-lactam (including penicillins and cephalosporins) antibiotic-producing cell.

Plasmid pPS97 comprises the coding sequence of the ACV synthetase gene of *Cephalosporium acremonium*. Plasmid pPS97 or fragments derived therfrom can be used to construct vectors for increasing the copy number of the ACV synthetase gene and thus for increasing the intracellular concentration of the enzyme. Because the ACV synthetase coding sequence of the invention was isolated from a Cephalosporium host cell, the ACV synthetase coding sequence is particularly well-suited for use in expression vectors designed to drive high-level expression of ACV synthetase activity in Cephalosporium host cells.

The *C. acremonium* ACV synthetase coding sequence of the invention can also be put under the control of transcription and translation activating sequences derived from strains of Penicillium, as well as from Cephalosporium, or any other host cell to construct a recombinant ACV synthetase gene for use in the given organism.

ACV synthetase expression vectors that contain the acetamidase gene or the phleomycin resistance gene are particularly useful as vectors for inserting genes into *Penicillium chrysogenum* because no special recipient strain, such as an auxotroph, need be constructed, owing to the natural inability of *P. chrysogenum* to grow on acetamide as sole nitrogen source or in the presence of phleomycin. Transformation systems based on complementation of auxotrophic markers by a gene in the transforming plasmid do not share this advantage. Frequently, pleiotropic mutations are associated with the introduction of an auxotrophic marker into a *P. chrysogenum* strain highly developed for penicillin production. Such mutations usually result in lower penicillin production (MacDonald et al., 1963, *J. Gen. Microbiol.* 33:

365–374). The vectors described above and in the Examples are merely illustrative of the wide variety of ACV synthetase expression vectors provided by the present invention.

The DNA compounds of the present invention are derived from genomic DNA of *Cephalosporium acremonium* and are significantly homologous in nucleotide sequence to the DNA compounds encoding ACV synthetase activity in other cephalosporin-producing organisms, in bacteria such as *Streptomyces clavuligerus* or fungi such as *Aspergillus nidulans* and *Penicillium chrysogenum*. Because of this homology, the ACV synthetase-encoding DNA compounds of the present invention can be labelled and used to screen genomic libraries of organisms that produce beta-lactam or similar compounds for the presence of ACV synthetase-encoding DNA. Many organisms comprise ACV synthetase activity-encoding DNA that can be identified and isolated using the DNA compounds of the present invention, and the present invention comprises these equivalent, homologous DNA compounds.

Due to the degenerate nature of the genetic code, which results from there being more than one codon for most of the amino acid residues and translation stop signal, the amino acid residue sequence of ACV synthetase enzyme depicted above can be encoded by a multitude of different DNA sequences. Because these alternate DNA sequences would encode the same amino acid residue sequence of the present invention, the present invention further comprises these alternate sequences.

The present invention provides the starting material for a search for a mutant ACV synthetase that can accept alternative substrates or which is more active. The invention comprises DNA compounds derived through mutagenesis of an ACV synthetase coding sequence. *E. coli* is the best host for mutational cloning experiments, and the *E. coli* expression vectors of the present invention can be readily mutated by procedures well known in the art, such as, for example, treatment with radiation (X-ray or UV) or chemical mutagens (such as ethyl methanesulfonate, nitrosoguanidine, or methyl methanesulfonate) or site-specific mutagenesis, to obtain mutant enzymes that recognize alternative substrates and catalyze the conversion of those substrates to novel compounds.

The following Examples are provided to further illustrate and exemplify, but do not limit the scope of, the present invention.

EXAMPLE 1

Source of the Cephalosporium ACV Synthetase Gene

A. Culture of *E. coli* K12 DH5α/pPS97

A lyophil of *E. coli* K12 DH5α/pPS97 can be obtained from the Northern Regional Research Laboratories (NRRL), Peoria, Ill. 61604, under the accession number NRRL B-18653 and used directly as the "culture" in the process described below.

Figure 2:
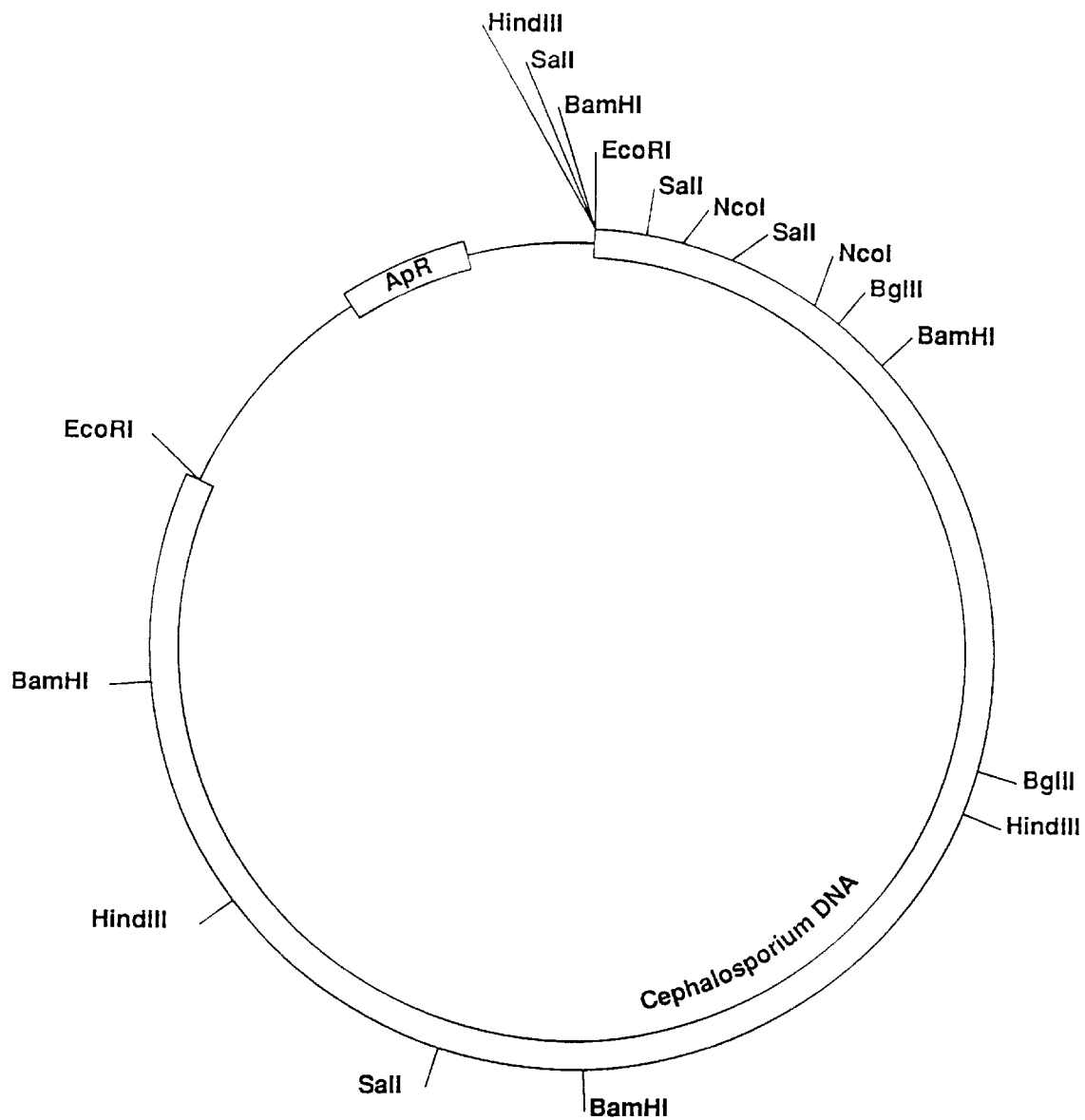
FIG. 2. A restriction site and function map of plasmid pPS97.
Figure 3:
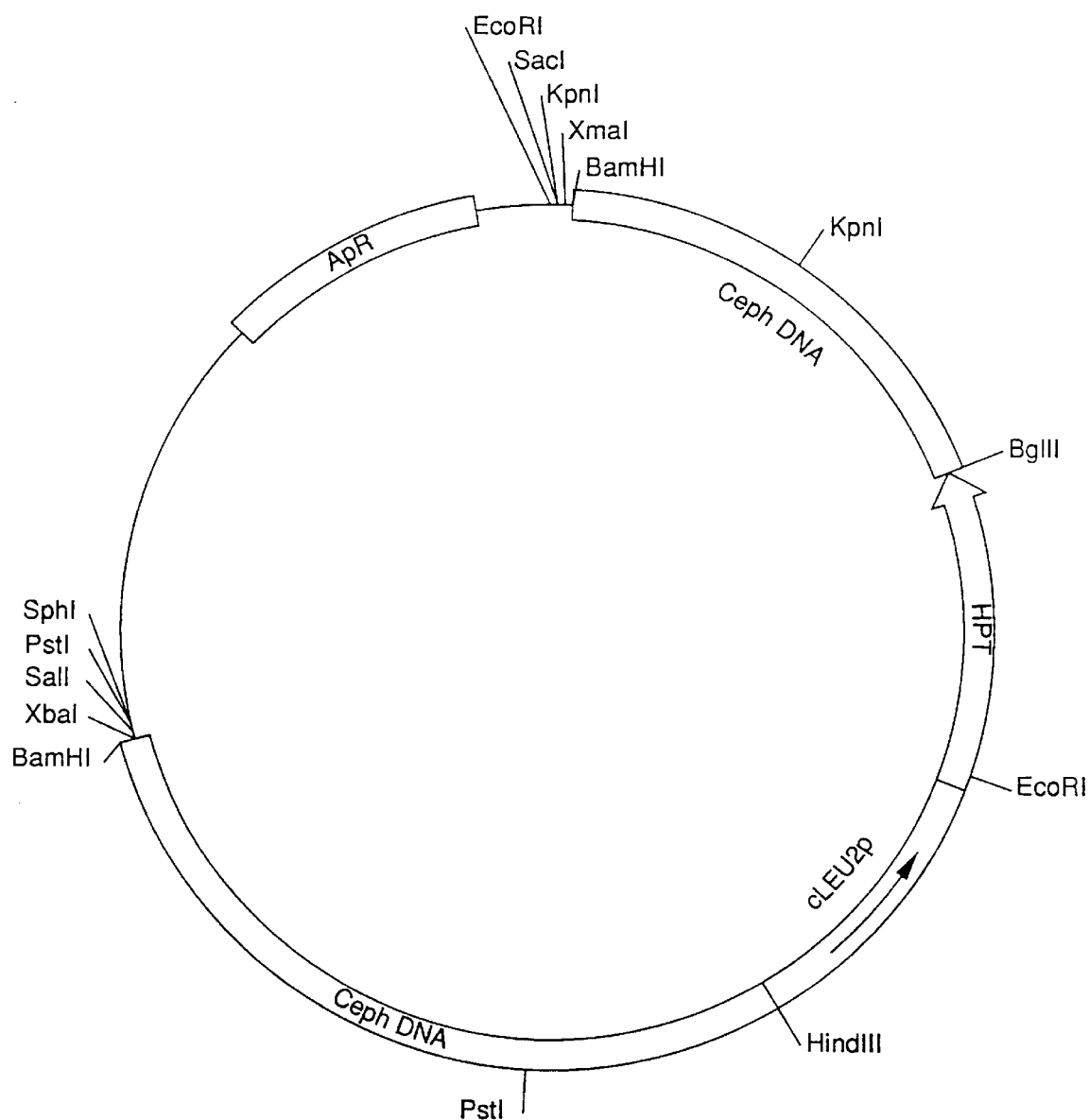
FIG. 3. A restriction site and function map of plasmid pPS96.

One liter of TY broth (10 g tryptone, 5 g NaCl, and 5 g yeast extract per liter) containing 100 $\mu$g/ml ampicillin was inoculated with a culture of *E. coli* K12 DH5α/pPS97 and incubated with aeration at 37° C. overnight (15–18 hours). The resulting culture was used as a source of plasmid pPS97 (FIG. 2).

B. Isolation of Plasmid pPS97

The culture prepared in Example 1A was centrifuged at 5200 rpm in a Sorvall GSA rotor (DuPont, Instrument Products, Biomedical Division, Newtown, Conn. 06470) for 10 minutes at 4° C. to pellet the cells. The resulting supernatant was discarded. The cell pellet was resuspended in 28 ml of a solution of 25% sucrose and 50 mM ethylenediamine tetraacetic acid (EDTA). About 1 ml of a solution of 20 mg/ml lysozyme in 50% glycerol and 0.25 M Tris-HCl (Tris (hydroxymethyl)-aminomethane hydrochloride), pH=8.0, and about 1.5 ml of 0.5 M EDTA, pH=8.0, were added to and mixed with the cell suspension. The resulting mixture was incubated on ice for 15 minutes. Three ml of lysing solution (prepared by mixing 3 ml of 10% Triton X-100; 75 ml of 0.25 M EDTA, pH=8.0; and 7 ml of water) were added to the lysozyme-treated cells with gentle mixing. The resulting solution was incubated on ice for another 15 minutes.

The cellular debris was removed from the solution by centrifugation at 17,000 rpm in a Sorvall SS34 rotor (DuPont, Instrument Products, Biomedical Division, Newtown, Conn. 06470) for about 45 minutes at 4° C. About 28.6 g of CsCl and ~1 ml of a 5 mg/ml ethidium bromide solution were added to the ~30 ml of supernatant. Then, the volume was adjusted to 40 ml with water and the solution decanted into an ultracentrifuge tube. The tube was sealed, and the solution was centrifuged at 49,500 rpm in a Ti70 rotor (Beckman, 7360 N. Lincoln Avenue, Lincolnwood, Ill. 60646) for ~18 hours. The resulting plasmid band, visualized with ultraviolet light, was isolated, extracted with CsCl-saturated isopropanol to remove the ethidium bromide, and dialysed against three changes of ~20 volumes of TE buffer (10 mM Tris-HCl pH=7.5, and 1 mM EDTA). The dialysate was collected; then, two volumes of ethanol and 0.05 volumes of 3 M sodium acetate solution were added. The ethanol mixture was cooled to –20° C., and the plasmid DNA was pelleted by centrifugation at 10,000 rpm in an SS34 rotor for 30 minutes at –10° C. The resulting pellet was resuspended in ~1 ml of TE buffer and then extracted with an equal volume of a phenol:chloroform mixture (1:1, v/v). The DNA in the aqueous phase was recovered by the addition of 0.1 volume of 3 M sodium acetate and 2 volumes of ethanol, followed by incubation at –20° C. for ~30 minutes and centrifugation at 15,000 rpm in an SS34 rotor for 20 minutes. The resulting DNA pellet was rinsed first with 70% ethanol and then with 100% ethanol and dried.

The ~1.5 mg of plasmid pPS97 DNA obtained by this procedure was suspended in 1.5 ml of 0.1×TE buffer and stored at –20° C. A restriction site and function map of plasmid pPS97 is presented in FIG. 2 of the accompanying drawings.

EXAMPLE 2

Construction of Intermediate Plasmid pRH5

A. Source of Phleomycin and a Plasmid Containing a Phleomycin Resistance Gene

Figure 5:
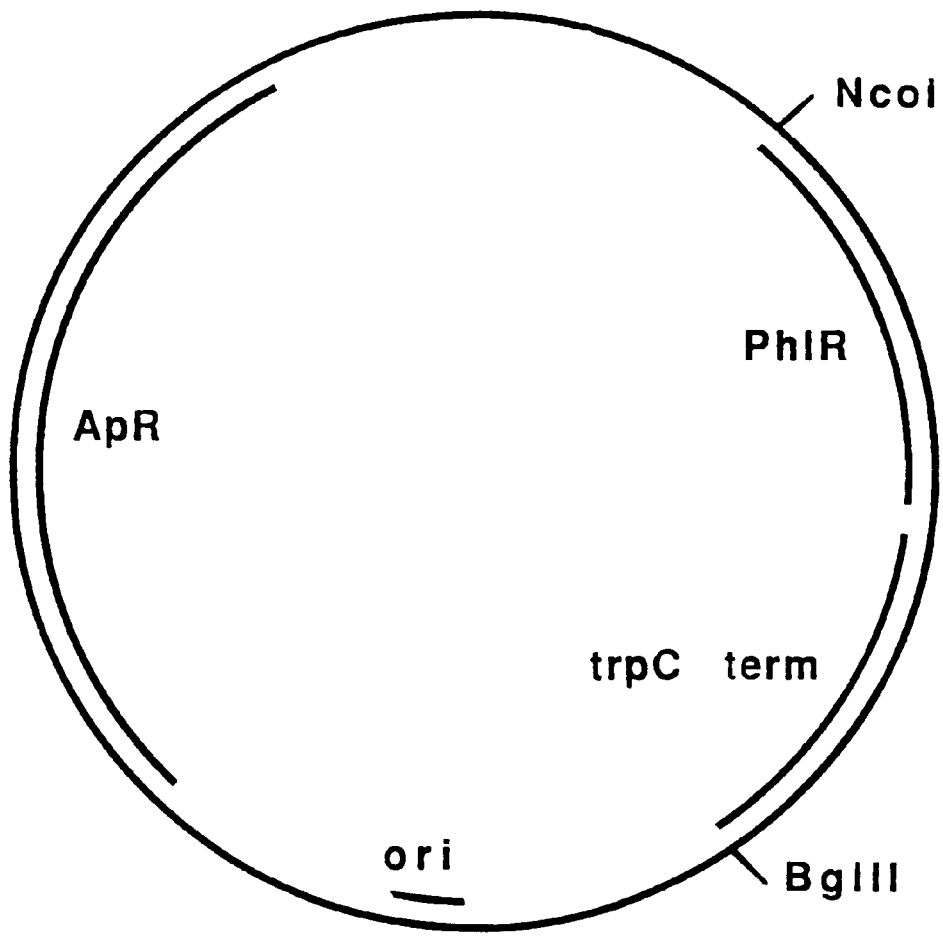
FIG. 5. A restriction site and function map of plasmid pUT715.

Phleomycin was purchased from Cayla, Avenue De Larrieu, 31094 Toulouse, Cedex, France. Plasmid pUT715 which contains a *Streptoalloteichus hindustanus* phleomycin resistance gene juxtaposed to the 3' regulatory DNA sequence of the *Aspergillus nidulans* trpC gene (trpC term), was also obtained from Cayla. A restriction map and function map of pUT715 is presented in FIG. 5 of the accompanying drawings.

B. Source of the *Penicillium Chrysogenum* IPNS Promoter

Figure 6:
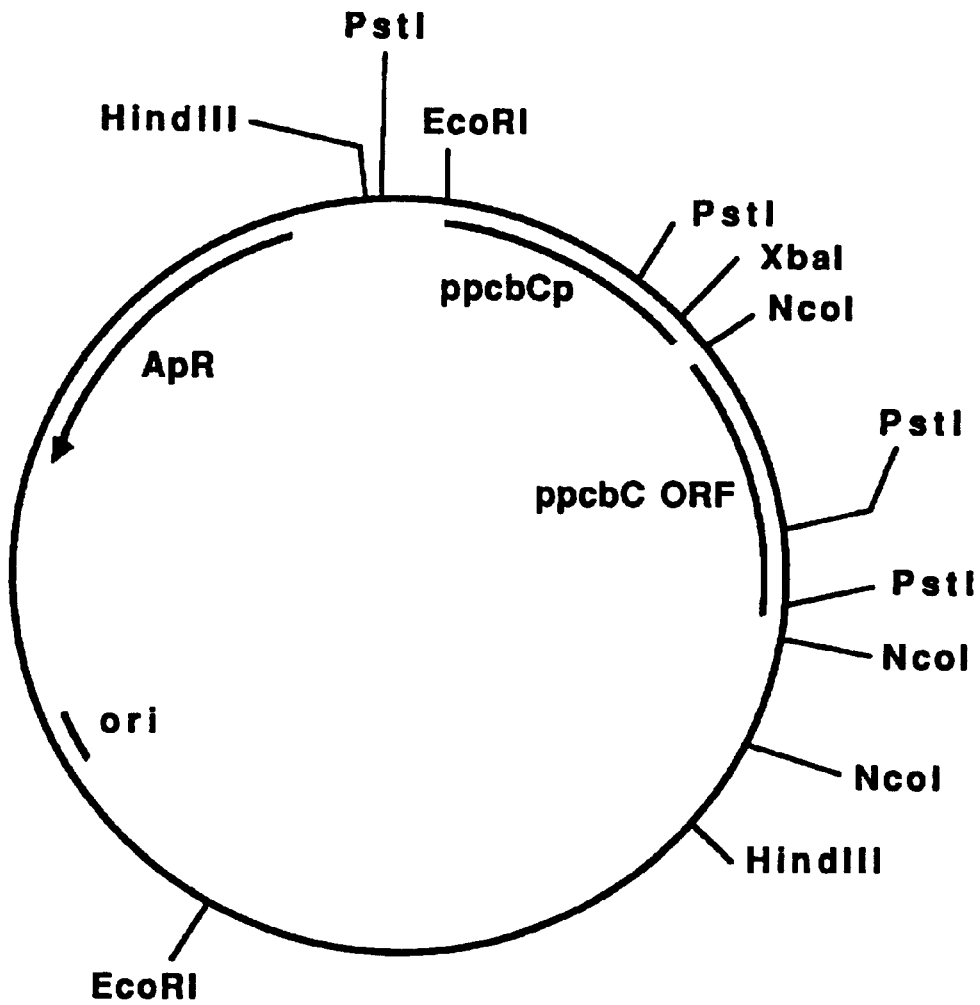
FIG. 6. A restriction site and function map of plasmid pLC2.

The promoter of the IPNS gene is located within the approximately 0.9 kb of DNA immediately upstream of the *Penicillium chrysogenum* IPNS coding region, bounded by the restriction sites EcoRI and NcoI, in plasmid pLC2 (pXL2 in Carr et al., Gene 48:257–266 (1986)). Plasmid pLC2 may be obtained from the American Type Culture Collection (Rockville, Md. 20852) under accession number ATCC 53334 and isolated in substantial accordance with the procedure of Example 1. A restriction map and function map of plasmid pLC2 is presented in FIG. 6 of the accompanying drawings. The ~0.9 kb EcoRI-NcoI restriction fragment containing the IPNS promoter was isolated from plasmid pLC2 as described below.

The plasmid pLC2 was digested to completion with EcoRI and NcoI as follows. Five µl (~5 µg) of plasmid pLC2 DNA as prepared above are mixed with 38 µl of $H_2O$, 5 µl of 10× EcoRI and NcoI restriction buffer (500 mM Tris-HCl (pH 8.0), 100 mM $MgCl_2$, and 1 M NaCl), and 1 µl each of restriction enzymes EcoRI and NcoI (~8 units, Bethesda Research Laboratories, Inc., P.O. Box 577, Gaithersburg, Md. 20760). The reaction mixture was incubated for 2 hours at 37° C. The digestion products were then electrophoresed on a 1% agarose gel until the desired ~0.9 kb EcoRI-NcoI restriction fragment was clearly separated from the other digestion products. The electrophoresed DNA was visualized by staining the gel in a dilute solution (0.5 µg/ml) of ethidium bromide and exposing the stained gel to long-wave UV light. After the fragments were located, a small slit was made in the gel in front of the ~0.9 kb fragment, and a piece of Schleicher and Schuell (Keene, N.H. 03431) DEAE membrane was placed in the slit. Upon further electrophoresis, the DNA non-covalently bound to the DEAE membrane. After the desired fragment was bound to the DEAE membrane, the membrane was removed and rinsed with low salt buffer (100 mM NaCl; 0.1 mM EDTA; and 20 mM Tris-HCl, pH 8). Next, the membrane was placed in a small tube and immersed in high salt buffer (1 M NaCl; 0.1 mM EDTA; and 20 mM Tris-HCl, pH 8) and then incubated at 65° C. for 10 minutes to remove the DNA from the DEAE paper. After the 65° C. incubation, the incubation buffer was collected, and the membrane was rinsed with high salt buffer. The rinse solution was pooled with the incubation buffer before collecting the desired DNA fragments.

The volume of the high salt-DNA solution was adjusted so that the NaCl concentration was 0.25 M, and then three volumes of cold, absolute ethanol were added to the solution. The resulting solution was mixed and placed on ice for 10–20 minutes. The solution was then centrifuged at 15,000 rpm in an SS34 rotor for 15 minutes. After another precipitation to remove residual salt, the DNA pellet was rinsed with 70% ethanol, dried, resuspended in 20 µl of TE buffer, and constituted the desired restriction fragment.

C. Source of Plasmid pKC787

Figure 7:
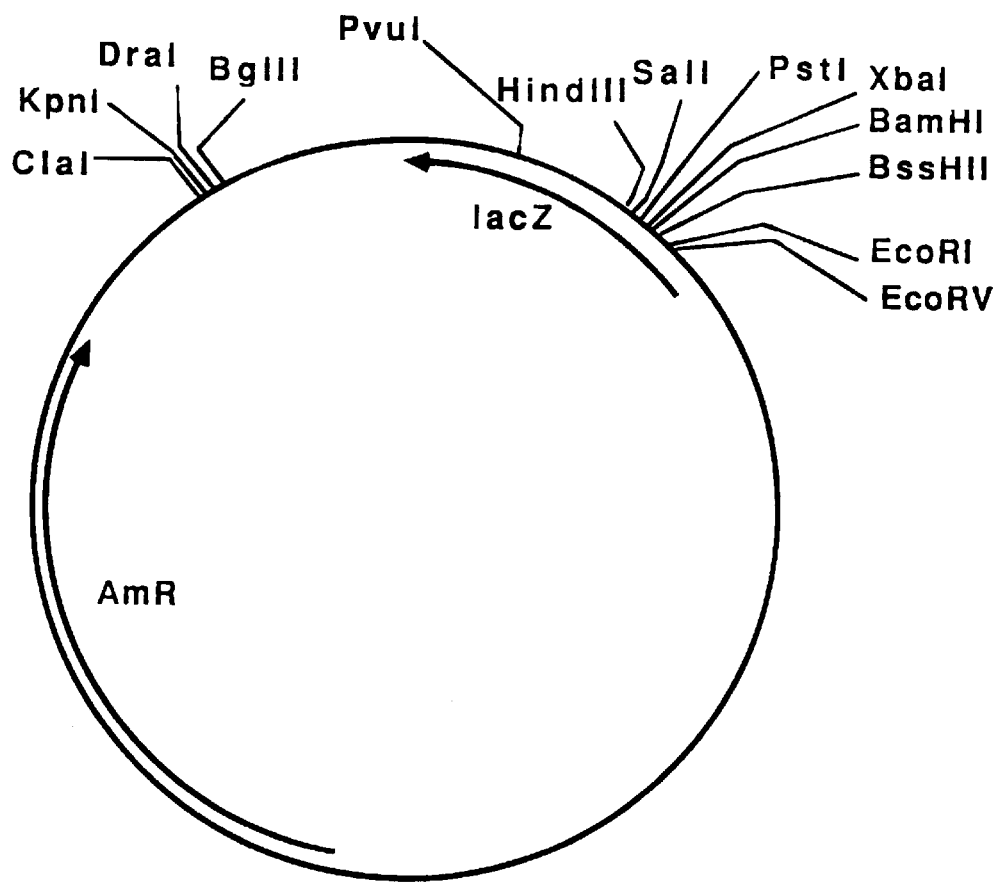
FIG. 7. A restriction site and function map of plasmid pKC787.

Plasmid pKC787 provided the apramycin resistance gene for selection of transformants in *E. coli* and the *E. coli* origin of DNA replication for the final construction. An *E. coli* strain carrying plasmid pKC787 may be obtained from the NRRL under accession number NRRL B-18516 (date of deposit: Jun. 30, 1989) and the plasmid isolated in substantial accordance with the teaching of Example 1. A restriction map and function map of plasmid pKC787 is presented in FIG. 7 of the accompanying drawings.

D. Construction of plasmid pRH5

Approximately 5 µg of plasmid pKC787 were cut to completion with the restriction enzymes EcoRI and BamHI in substantial accordance with the teaching of Example 2B except that restriction enzyme BamHI was used instead of NcoI. Approximately 5 µg of plasmid pUT715 were cut to completion with the restriction enzymes NcoI and BglII in substantial accordance with the teaching of Example 2B except that restriction enzyme BglII was used instead of EcoRI. Restriction enzymes involved in these reactions were inactivated by extraction with phenol and chloroform, followed by ethanol precipitation. Approximately 0.2 µg of EcoRI/BamHI cut pKC787 DNA, ~0.2 µg of NcoI/BglII cut pUT715 DNA (FIG. 5), and ~0.2 µg of the 0.9 kb EcoRI to NcoI fragment containing the *Penicillium chrysogenum* IPNS promoter from plasmid pLC2 (purification of this fragment was described in section B above) were mixed and ligated in the presence of T4 DNA ligase. The ligation mixture included the DNA fragments, 10 µl of 10× ligase buffer (0.5 M Tris-HCl, pH 7.5 and 100 mM $MgCl_2$), 10 µl 0.1 mM adenosine triphosphate (ATP), 10 µl of 0.1 M DTT, 1 µl T4 DNA ligase (1 unit, Boehringer-Mannheim Biochemicals (BMB), 7941 Castleway Drive, P.O. Box 50816, Indianapolis, Ind. 46250) and enough water for a total volume of 100 µl . The mixture was incubated at 14° C. overnight. The ligation mixture was transformed into *E. coli* K12 JM109 as follows. Competent *E. coli* K12 JM109 ("*Epicurean Coli*™") were purchased from Strategene (3370 Tansy Street, San Diego, Calif. 92121) and transformed with a ligation reaction mixture comprising plasmid pRH5. The ligated DNA was mixed with 100 µl of competent JM109 cells, incubated for one hour on ice, then incubated for one minute at 42° C., then diluted with 2 ml of fresh TY broth and incubated at 37° C. for one hour. Aliquots of the transformation mixture were plated on TY-agar plates containing 100 µg/ml apramycin.

Figure 8:
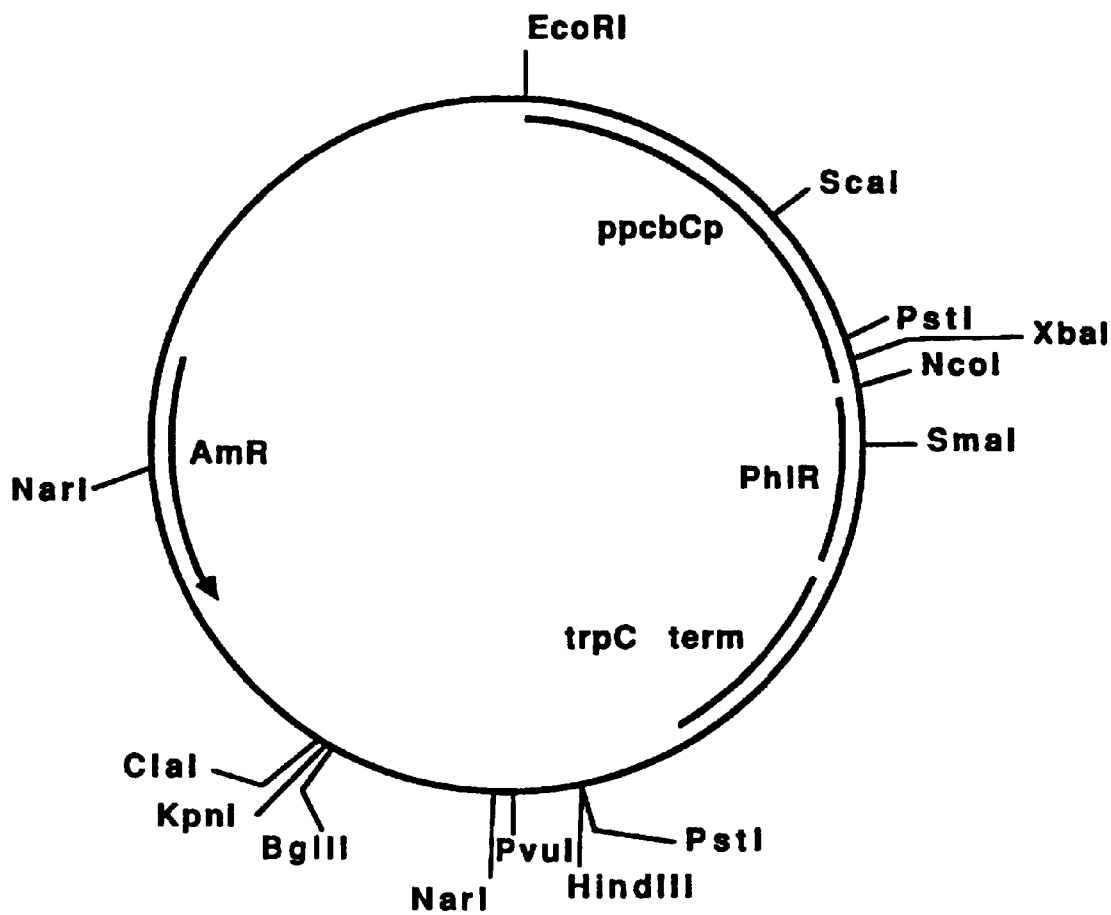
FIG. 8. A restriction site and function map of plasmid pRH5.
Figure 9:
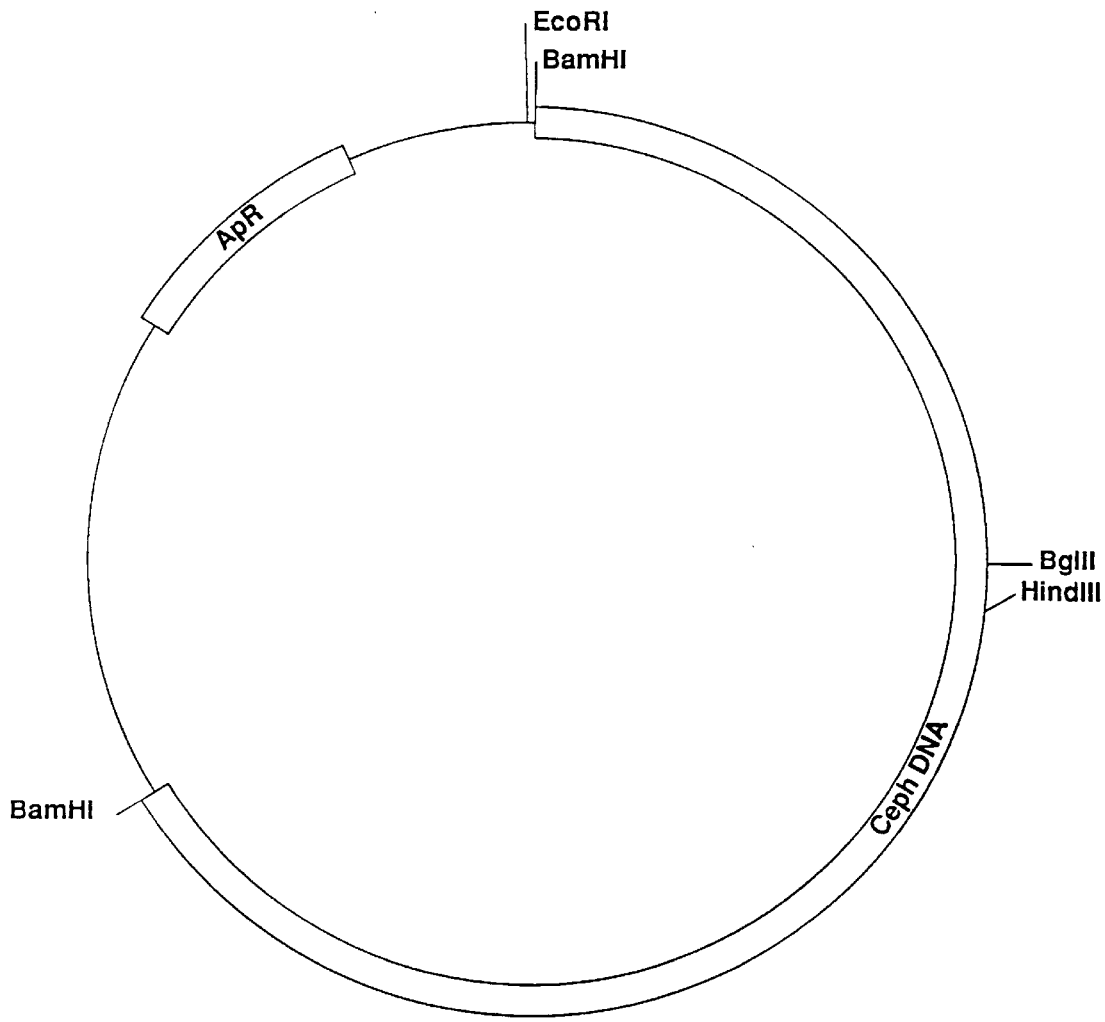
FIG. 9. A restriction site and function map of plasmid pPS81.

Apramycin resistant transformants were screened for sensitivity to ampicillin. Apramycin resistant, ampicillin sensitive transformants were screened for the presence of a plasmid containing fragments in the proper orientation as shown in FIG. 8. A transformant carrying the described plasmid was isolated and the plasmid is designated pRH5. A restriction site and function map of plasmid pRH5 is presented in FIG. 8 of the accompanying drawings.

EXAMPLE 3

Isolation of Fragments for the Construction of Plasmid pZAZ3

A. Isolation of the ~3.8 kb EcoRI/NcoI Fragment from Plasmid pRH5

Plasmid pRH5 (constructed in Example 2) was isolated from *E. coli* K12 JM109/pRH5 in accordance with the method of Example 1. Approximately 5 µg of plasmid pRH5 were cut to completion with the restriction enzymes NcoI and EcoRI as follows. Five µl (5 µg) of plasmid pRH5 were mixed with 5 µl 10× buffer (500 mM Tris-HCl (pH 8.0), 100 mM $MgCl_2$, and 1M NaCl), 1 µl EcoRI (8–12 units, BRL), 1 µl NcoI (1–8 units, BRL) and 38 µl $H_2O$. The reaction was incubated at 37° C. for 1 hour. The desired ~3.8 kb NcoI/EcoRI restriction fragment was separated and isolated by agarose gel electrophoresis in substantial accordance with the method of Example 2B. The purified fragment was then dissolved in about 100 µl of TE buffer and stored at −20° C. for future use.

B. Isolation of the ~0.7 kb NcoI/PstI Fragment from Plasmid pIT335

Plasmid pIT335 was isolated from *E. coli* K12 JA221/pIT335, available from the NRRL under accession number B-15960, in substantial accordance with the teaching of Example 1. Approximately 5 µg of plasmid pIT335 were cut to completion with the restriction enzymes NcoI and PstI as follows. Five µl (~5 µg) of plasmid pIT335 were mixed with 1 µl PstI (8–12 units, BRL) and 1 µl NcoI (1–8 units, BRL) in 100 µl of 50 mM NaCl, 50 mM Tris 8.0, 10 mM $MgCl_2$, and 100 µg/ml BSA. The reaction was incubated at 1 hour for 37° C. The desired ~0.7 kb NcoI/PstI restriction fragment, which contains the *Cephalosporium acremonium* isopenicillin N synthetase gene promoter, was separated and isolated by agarose gel electrophoresis in substantial accordance with the method of Example 2B. The purified fragment was then resuspended in about 100 µl of TE buffer and stored at −20° C. for future use.

C. Construction of an EcoRI/PstI DNA Linker

The desired linker has the following sequence:

5' AATTCTGCA 3'

It can be conventionally synthesized by the modified phosphotriester method in substantial accordance with the teaching of Itakura et al., *Science* 198:1056 (1977) and Crea et al., *Proc. Nat'l Acad. Sci. USA* 75:5765 (1978).

EXAMPLE 4

Final Construction of Plasmid pZAZ3

About 20 picomoles of the synthetic DNA linker created in Example 3C were ligated to ~0.5 µg of the ~0.7 kb NcoI/PstI fragment isolated from plasmid pIT335 and ~0.5 µg of the ~3.8 kb NcoI/EcoRI fragment isolated from plasmid pRH5. The ligation mixture was diluted 1:50 in water, then 5 µl of the diluted mixture were placed in a 1.8 ml Eppendorf™ tube. Forty µl of *E. coli* DH5α (1×10$^{10}$ cells/ml) were added to the tube with mixing. The mixture was transferred to a curvet and subjected to current produced by a Bio-Rad Genepulse™ system set at 2.25 kV electrical potential difference, 25 µFD capacitance, 200 Ω resistance. After treatment, the cells were immediately transferred to SOC medium (L broth supplemented with 2.5 mM KCl, 10 mM MgCl$_2$, 10 mM MgSO$_4$ and 20 mM glucose). The cells were incubated for 1 hour at 37° C. Aliquots of the electroporation mixture were plated on TY agar plates containing 100 µg/ml apramycin.

Some of the resultant transformants, as shown by restriction enzyme analysis of plasmid DNA isolated from the transformants, contained only the desired ~4.5 kb pZAZ3 plasmid. Such a transformant, herein designated *E. coli* K12 DH5α/pZAZ3, was selected on TY agar (TY broth+15 g/liter agar) containing apramycin at 100 µg/ml and then cultured using conventional microbiological techniques. The resultant transformants were used to isolate plasmid pZAZ3, as described in Example 1.

EXAMPLE 5

Construction of Plasmid pZAZ4

Approximately 10 µl (10 µg) of plasmid pZAZ3, constructed in Example 4, were digested with EcoRI as follows. The plasmid was mixed with 5 µl 10× EcoRI buffer (500 mM Tris-HCl (pH 8.0), 100 mM MgCl$_2$, and 1M NaCl), 1 µl EcoRI (8–12 units, BRL), and 34 µl H$_2$O. The reaction was incubated at 37° C. for 1 hour. The 5' ends of the digested plasmid were then dephosphorylated in accordance with the procedure detailed in J. Sambrook, E. F. Fritsch & T. Maniatis, *Molecular Cloning: A Laboratory Manual* 1.60–0.61 (1989).

Figure 4:
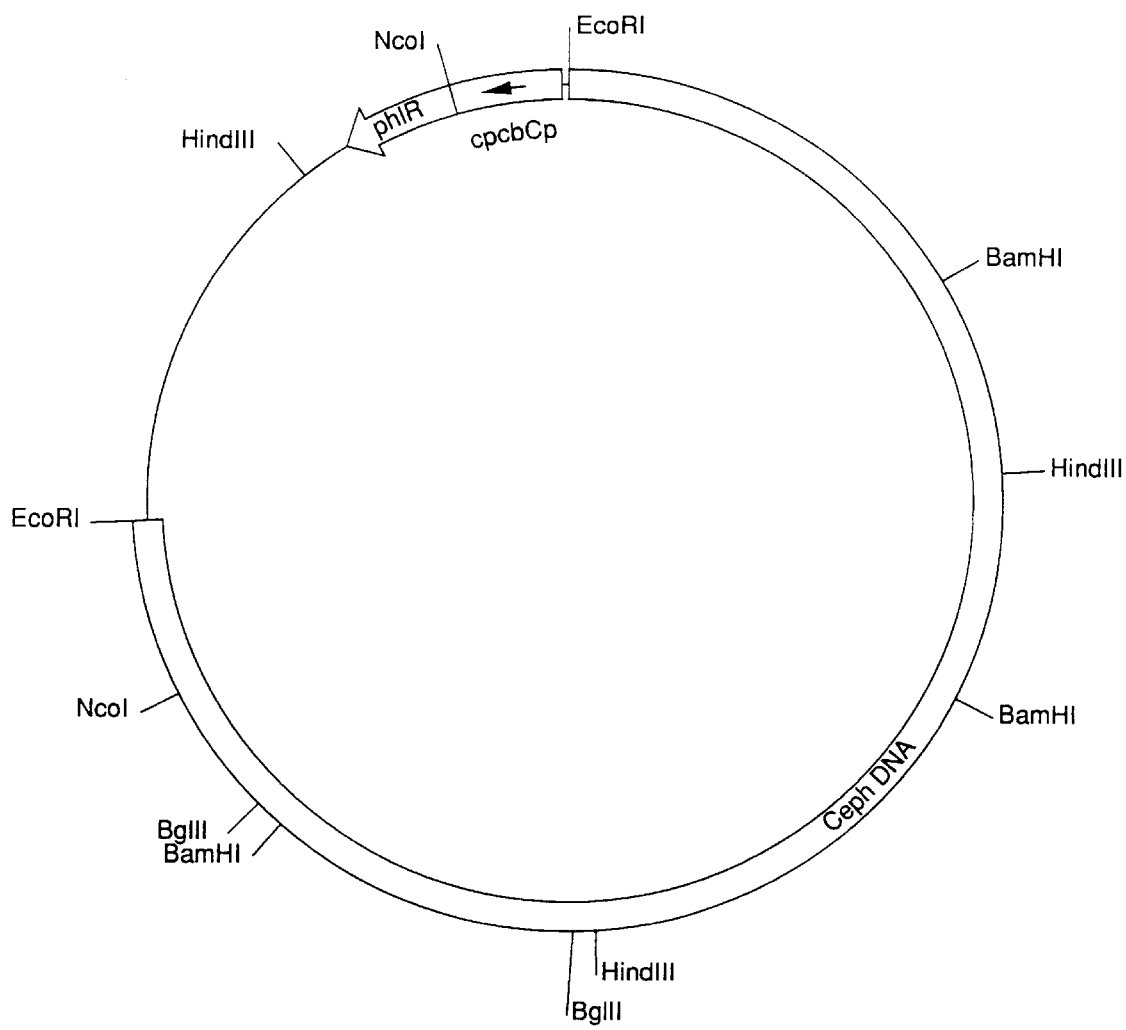
FIG. 4. A restriction site and function map of plasmid pZAZ4.

About 10 µg of plasmid pPS97 (isolated in Example 1) were digested with EcoRI as described above. The resultant material was then run over an ~0.8% agarose gel and the ~13.7 kb band was isolated as described in Example 2B. The band comprised the ACV synthetase coding region. The EcoRI-digested plasmid pZAZ3 and the ~13.7 kb EcoRI fragment isolated from plasmid pPS97 were ligated and the resultant material transformed into *E. coli* K12 DH5α in substantial accordance with the procedure of Example 4. Apramycin-resistant transformants were analyzed by restriction digestion to determine if they contained desired plasmid pZAZ4. A restriction site and function map of plasmid pZAZ4 is presented in FIG. 4 of the drawings.

EXAMPLE 6

Increased Levels of ACV Synthetase Enzyme in *Cephalosporium acremonium* by Gene Dosage A. Transformation of Cephalosporium with Plasmid pZAZ4

Plasmid pZAZ4 is an ACV synthetase expression vector constructed for use in a Cephalosporium host. The intracellular concentration of ACV synthetase activity in *Cephalosporium acremonium* can be increased by the presence of additional ACV synthetase genes as provided by plasmid pZAZ4.

Preparation of Cephalosporium protoplasts and transformation of a *Cephalosporium acremonium* strain using plasmid pZAZ4 is accomplished with the procedure of U.S. Pat. No. 4,762,786, herein incorporated by reference.

After transformation, protoplasts are plated on selective medium (Trypticase Soy Agar, BBL Micro-biology Systems, Becton Dickinson and Co., Cockeysville, Md. 21030) containing 1 µg/ml phleomycin. Incubation at 28° C. thereafter yields transformants in about 4–7 days.

B. Analysis of Cephalosporin Transformants and Detection of Cephalosporin Production Cephalosporium transformants exhibiting stable phleomycin resistance can be subsequently picked and transferred to a medium able to support active cephalosporin C synthesis, such as 3.9% beet molasses, 0.65% CaCO$_3$, 0.1% Ca(OH)$_2$, 3.6% fish meal, 3.9% peanut meal, 1.0% CaSO$_4$, 10% lard oil, and 0.5% (NH$_4$)$_2$SO$_4$ (for strains unable to utilize sulfate efficiently as a sulfur source, (NH$_4$)$_2$SO$_4$ is replaced with 1% DL-methionine). Cells were grown at 28° C. for 7–10 days. Cell-free extracts can be prepared according to the method of Dotzlaf, J. E. and Yeh, W.-K., *J. Bacteriol.* 169:1611 (1986), and assayed for ACV synthetase as described by van Liempt et al., *J. Biol. Chem.* 264:3680 (1989).

For those strains of *C. acremonium* in which ACV synthetase represents a rate-limiting step, improvement of cephalosporin C production can result by the expression of extra copies of the ACV synthetase gene stably integrated into the strain's genome. Cephalosporin C is an important intermediate in the manufacture of parenteral cephalosporin antibiotics.

Cephalosporin C present in fermentation broths is measured by HPLC separation of broth components and UV analysis using procedures described in Dotzlaf and Yeh, supra, for deacetoxycephalosporin C and deacetylcephalosporin C. The results are compared to known quantities of cephalosporin C analyzed in the same manner.

We claim:

1. A DNA compound consisting essentially of an isolated DNA sequence encoding ACV synthetase activity of *Cephalosporium acremonium*, wherein said DNA compound is the ~12 kb EcoRI-SalI restriction fragment of plasmid pPS97.

2. A recombinant DNA vector that comprises the isolated DNA sequence of claim 1.

3. The recombinant DNA vector of claim 2 that is selected from the group consisting of plasmid pPS97 and pZAZ4.

4. A recombinant host cell transformed with a recombinant DNA vector of claim 2.

5. A recombinant DNA vector of claim 2 that further comprises a promoter and translational activating sequence positioned to drive expression of said ACV synthetase activity-encoding DNA.

6. The recombinant DNA vector of claim 3 that is pPS97.

7. The recombinant DNA vector of claim 3 that is pZAZ4.

8. The recombinant DNA vector of claim 7, wherein said promoter and translational activating sequence function in *E. coli*.

9. The recombinant DNA vector of claim 7, wherein said promoter and translational activating sequence function in Aspergillus.

10. The recombinant DNA vector of claim 7, wherein said promoter and translational activating sequence function in Penicillium.

11. The recombinant DNA vector of claim 7, wherein said promoter and translational activating sequence function in Cephalosporium.

12. The recombinant DNA vector of claim 8, wherein said promoter is the λ pL promoter.

13. The recombinant DNA vector of claim 10, wherein said promoter is the promoter of the *Penicillium chrysogenum* IPNS gene.

14. The recombinant DNA vector of claim 11, wherein said promoter is the promoter of the *Cephalosporium acremonium* DAOCS/DACS gene.

15. The recombinant DNA vector of claim 11, wherein said promoter is the promoter of the *Cephalosporium acremonium* IPNS gene.

16. A method of using a recombinant DNA vector that comprises the isolated DNA sequence of claim 1, said method comprising transforming a host cell with said DNA vector.

17. The method of claim 16, wherein said host cell is selected from the group consisting of *E. coli*, Aspergillus, Cephalosporium, and Penicillium.

18. The method of claim 16, wherein said recombinant host cell expresses an increased amount of ACV synthetase activity as compared to the untransformed host cell.

19. A method of using the transformed host cell of claim 16, said method comprising culturing said transformed host cell under conditions suitable for gene expression.

20. The method of claim 17, wherein said host cell is *E. coli*.

21. The method of claim 17, wherein said host cell is Penicillium.

22. The method of claim 17, wherein said host cell is Aspergillus.

23. The method of claim 17, wherein said host cell is Cephalosporium.

24. The method of claim 18, wherein said host cell is Cephalosporium.

25. A method for using the transformed host cell of claim 18, said method comprising culturing said transformed host cell under conditions suitable for gene expression.

26. The transformed host cell of claim 4 that is *E. coli* K12.

27. The transformed host cell of claim 4 that is Penicillium.

28. The transformed host cell of claim 4 that is Aspergillus.

29. The transformed host cell of claim 27 that is *Penicillium chrysogenum*.

30. The method of claim 19, wherein said host cell is *E. coli*.

31. The method of claim 19, wherein said host cell is Penicillium.

32. The method of claim 19, wherein said host cell is Aspergillus.

33. The method of claim 19, wherein said host cell is Cephalosporium.

34. A DNA compound that consists of an isolated DNA sequence encoding ACV synthetase activity of *Cephalosporium acremonium*, wherein said DNA compound is the ~12 kb EcoRI-SalI restriction fragment of plasmid pPS97.

* * * * *